United States Patent [19]
Takaichi et al.

[11] Patent Number: 5,174,987
[45] Date of Patent: Dec. 29, 1992

[54] METHOD OF USING IRON CONTAINING PREPARATION FOR NMR IMAGING

[75] Inventors: Akihisa Takaichi; Toshihiko Okamoto; Toshiaki Matsumoto, all of Tokushima; Junji Nakamura, Nara; Toshio Nakamura, Tokushima, all of Japan

[73] Assignee: Otsuka Pharmaceutical Co., Ltd., Tokyo, Japan

[21] Appl. No.: 476,438

[22] PCT Filed: Oct. 3, 1989

[86] PCT No.: PCT/JP89/01009
§ 371 Date: Jun. 4, 1990
§ 102(e) Date: Jun. 4, 1990

[87] PCT Pub. No.: WO90/03800
PCT Pub. Date: Apr. 19, 1990

[30] Foreign Application Priority Data

Oct. 4, 1988 [JP] Japan ............... 63-250664
Sep. 27, 1989 [JP] Japan ............... 1-252895

[51] Int. Cl.$^5$ ............... G01N 24/00; G01N 31/00; A61L 9/04; A61K 33/00
[52] U.S. Cl. ............... 424/9; 424/44; 424/647; 424/648; 424/700; 424/715; 424/717; 436/173; 128/653.4
[58] Field of Search ............... 424/9, 646, 647, 648, 424/44, 715, 717, 700; 436/173; 128/653 AF, 654

[56] References Cited

U.S. PATENT DOCUMENTS

| | | | |
|---|---|---|---|
| 3,794,722 | 2/1974 | Taya | 424/647 |
| 3,829,561 | 8/1974 | Heinrich | 424/44 |
| 4,036,228 | 7/1977 | Theeuwes | 424/473 |
| 4,083,951 | 4/1978 | Goudie et al. | 424/44 |
| 4,615,879 | 10/1986 | Runge | 424/9 |
| 4,675,173 | 6/1987 | Widder | 424/9 |
| 4,719,098 | 1/1988 | Weinmann | 424/9 |
| 4,725,427 | 2/1988 | Ashmead et al. | 424/44 |
| 4,752,479 | 6/1988 | Briggs et al. | 422/472 |
| 4,786,518 | 12/1988 | Nakel et al. | 426/531 |

OTHER PUBLICATIONS

Wesbey, G. E. Radiology 149:175-180 (1983).
Supplementary Partial European Search Report.

*Primary Examiner*—Richard L. Raymond
*Assistant Examiner*—Gary E. Hollinden
*Attorney, Agent, or Firm*—Sughrue Mion Zinn Macpeak & Seas

[57] ABSTRACT

There is described an iron containing preparation for NMR imaging comprising, as necessary ingredients, the prescribed amounts of an iron containing compound, sodium carbonate or sodium hydrogencarbonate and a neutralizing agent. This preparation is safe, easy to drink, and when taking, provides clear and accurate contrast imaging of inner organs. Further, addition of potassium carbonate to this preparation gives excellent preservation stability.

24 Claims, 5 Drawing Sheets

5,174,987

METHOD OF USING IRON CONTAINING PREPARATION FOR NMR IMAGING

TECHNICAL FIELD

This invention relates to a iron containing preparation for NMR imaging and to an NMR imaging method using the same. which preparation has a form such as a foaming tablet, powder or the like.

BACKGROUND OF THE INVENTION

Since the beginning of 1970, NMR (Nuclear Magnetic Resonance) is widely utilized as a medical diagnostic apparatus, especially as an imaging means capable of providing soft organization imagings having high resolution and contrast without using detrimental x-ray.

That is to say, many atoms have a certain property called as spin to which small magnetic moment is attached.

When the outer magnetic field does not exist, configuration of a magnetic moment is irregular, but in the presence of static magnetic field, nuclear magnetic moment takes precession to approximately the magnetic field direction. so that net alignment is generated in the magnetic field. NMR imaging method is achieved by using this priciple. According to NMR imgaging method, when a short radio frequency pulse is oscillated from a coil surrounding a patient which is set in a static magnetic field. a configuration based on the new magnetic field and precession in phase are generated by this pulse. On the other hand, when oscillation of the pulse is stopped. the above moment returns to the distribution of alignment and the irregular distribution of precession phase on the basis of the former static magnetic field. In such a case. detectable nuclear magnetic resonance is generated at the receiving coil, and by measuring such NMR signals, a proton density map of the objective tissue can be represented. Also, the NMR signal is largely depended with parameters of spin-lattice relaxation time ($T_1$, i.e. the time specific to return of nuclear magnetic moment to balance alignment in static magnetic field) and spin-spin relaxation time ($T_2$, i.e. the time specific to return the nuclear magnetic moment to the irregular precession phase distribution). Therefore, these mesurements can be applied to the diagnosis of pathogenic tissue states of a patient.

In NMR imaging method, it is known that physical parameters such as temperature, viscosity and hydration or the like of the tissue is effective to increase NMR signal strength or to change the contrast an NMR image. However, these methods are apparently not suitable for clinical applications. A method for enhancing the contrast of NMR images which is known in the present stage using a paramagnetic compound, as a contrast agent, which decreases spin-lattice relaxation time ($T_1$) at low concentration thereof, and decreases spin-spin relaxation time ($T_2$) at high concentration thereof. Contrast agents have been researched, and a typical example of such contrast agents are inorganic paramagnetic salts such as iron, manganese, chromium; or a organic chelate complex which consists of the paramagnetic metal ion mentioned above and one of various complex forming agents which are usually are aminopolycarbxylic acid such as ethylenediaminetetraacetic acid or diethy lenetriaminepentaacetic acid. The contrast agent is taken orally or otherwise in the form of a solution or a colloidal dispention liquid.

However, all of the known contrast agents which are suggested are found to be insufficient practically for use in NMR imaging methods, e.g., due to the difficulty in preparing such agents in a pharmaceutically acceptable form, a lack stability of the pharmaceutical form, difficulties in oral administration, poor taste, toxicity, or the like and, and ineffective viewing for using as a contrast agent, e.g. due to accuracy, clearness.

SUMMARY OF THE INVENTION

A object of the invention is to provide an iron containing preparation for NMR imaging, which is easily prepared in pharmaceutically acceptable form, and which has excellent solubility or dispersion in water so as to rapidly and easily dissolve or disperse in water, thereby being suitable for oral administration.

Another object of the present invention of the invention is to provide an iron containing preparation for NMR imaging, which has excellent storage stability.

Another object of the present invention of the invention is to provide an iron containing preparation for NMR imaging which is capable of accurately and clearly imaging abdominal organs by use as a contrast agent, and NMR imaging method using such a preparation.

According to this invention, there is provided an iron containing preparation for NMR imaging comprising, as essential ingredients, 0.1 to 10% by weight, as elemental iron, of an iron containing compound, 8 to 60% by weight of one or both selected from sodium carbonate and sodium hydrogen carbonate and 10 to 70% by weight of neutralizing agents.

DETAILED DESCRIPTION OF PREFERRED EMBODIMENTS

A preparation of this invention can be used in the form of tablet, granule, powder or capsule.

A preparation of this invention, especially in the form of powder or tablets, as excellent dissolution or dispersion properties in water. Therefore, an iron containing compound contained is easily dissolved or dispersed in water by merely putting the preparation into water, which generate carbonic acid gas (carbon dioxide) due to neutralization. Accordingly, a preparation is easily taken orally. Also, carbonic acid gas generated in the body of the patient makes the alimentary canal expand and extend, so that the form of alimentary canal, the state of lumen thereof and the relation between alimentary canal and other surrounding internal organs can be easily accomplished.

Furthermore, by taking a preparation of this invention, an extremely significant effect occurs such that signal strength of lumen of alimentary canal is enhanced so that imaging of the alimentary canal wall with enhanced contrast against adjacent abdominal organs such as pancreas and the like is achieved.

In addition, each ingredient in preparations of this invention is a safe material having low toxicity.

According to this invention, in order to improve preservation stability, there is provided iron containing preparations for NMR imaging comprising the above iron containing compound, and at least one of sodium carbonate and sodium hydrogen carbonate, the neutralizing agent and potassium carbonate as a preservation stabilizing agent.

Addition of potassium carbonate overcomes a disadvantage found in conventional foam preparations, i.e. foam or degeneration of product during preservation due to the existence of residual water resulting from the manufacturing process or hydration.

Examples of the iron containing compounds preferably employed in this invention are ammonium iron(II) citrate, ammonium iron(III) citrate, sodium iron(II) citrate, sodium iron(III) citrate, iron(II) citrate, iron(III) citrate, iron(II) gluconate, iron(II) pyrophosphate, iron(III) pyrophosphate, iron lactate, iron(II) sulfate, iron(III) chloride, iron sesquioxide, sodium iron chlorophyn, iron(II) fumarate, iron threonine, iron(II) orotinate, saccharated iron oxide, iron(III) gluconate or the like. These iron containing compounds are excellent in soluble and dispersive properties in water. These iron containing compounds are also used as an active component of a therapeutic agents for iron deficiency anemia, deficiency anemia, hematinic iron agent or the like in pharmaceutical field, and have high safety. In the iron containing compounds mentioned above, it is preferred to use trivalent iron salt, and especially it is most preferred to use trivalent citrate type, in view of safety and enhanced imaging (on contrast) effects, good taste and ease of drinking.

The iron containing compound is added in the form of a powder, the diameter of particles of which is ordinally not more than 200 μm. Each iron containing compound may be used alone or as a mixture of 2 or more kinds thereof. The amount of iron containing compound to be added is 0.1 to 10% by weight, preferably 0.5 to 5% by weight as elemental iron. Within this amount, the preparation of this invention achieves accurate and clear contrast effects in NMR imaging. This amount corresponds with about 10 to 300 mg, preferably about 25 to 100 mg per one preparation of the foam preparation of this invention.

At least one of sodium carbonate and sodium hydrogen carbon and a neutralizing agent are added as a foaming component, together with the above iron containing compound. The term neutralizing agent 11 means an acid compound capable of neutralizing sodium hydrogen carbonate and sodium bicarbonate to generate carbonic acid gas. Such a foam has the function of expanding and extending the alimentary canal, and therefore is very advantageous to know the form of alimentary canal and the state of its lumen from an NMR picture. Examples of such neutralizing agents are organic acids such as L-tartaric acid, citric acid, fumaric acid, lactic acid, malic acid or ascorbic acid, and it is especially preferred to use L-tartaric acid and/or citric acid.

The amount of the above foam component to be blended is provided such that the solution obtained by dissolving in water that is acidic, especially at a pH of about 3 to 5.5 of pH, preferably about 3.5 to 4.6 of pH, whereby the iron containing compound is rapidly dissolved in water. In particular, for example, the blending amount of each ingredient, sodium carbonate and/or sodium hydrogencarbonate is 8 to 60% by weight, and the neutralizing agent is 10 to 70% by weight. In the case where the preparation of this invention is used in the form of powder or the like, when the amount of sodium carbonate and/or sodium hydrogencarbonate is 20 to 60% by weight, excellent imaging effect is obtained, and when the amount of sodium carbonate and/or sodium hydrogen carbonate is 8 to 45% by weight, taste is improved so as to be agreeable to drink. Practically, it is therefore desirable for providing good taste and to facilitate admistration together with high imaging effect, that sodium carbonate is added at 9 to 50% by weight, preferably 22 to 26% by weight, and that sodium hydrogen carbonate is 8 to 50% by weight, preferably 20 to 45% by weight.

It is suitable that the neutralizing agent is added in the range of 20 to 50% by weight, preferably 30 to 40% by weight, and especially it is preferable to use at the same amount as or more than the equivalent amounts of sodium hydrogen carbonate.

According to this invention, in addition to sodium carbonate and/or sodium hydrogencarbonate and a neutralizing agent added as a foam component, it is preferred that potassium carbonate is added as a preservation stabilizing agent. That is to say, since sodium carbonate or sodium hydrogen carbonate are neutralized in the presence of water by a agent such as organic acid to generate carbonic acid gas and to promote the degradation and dissolution of the preparation, the preparation should be kept in a dry condition as much as possible so as to prevent foaming. There, however, a possibility of foaming during storage due to the presence of water remaining in preparing process or as hydration, even if it is preserved in a sealed container together with drying agent. If carbonic acid gas is generated during preservation, inner pressure of the sealed container is increased, and results in deformation or damage of the container, or can inhibit foaming when the product is used. Foaming during preservation is accelerated under a high temperature condition, and further the generated reaction water and carbonic acid gas accelerate the reaction.

It is now found that potassium carbonate is very effective to prevent foaming during preservation as mentioned above, and even if drying agent is not used during storage, foaming can be prevented. In view of securing a high stability of the preparation and easily taking it without lowering taste, it is suitable that potassium carbonate is added at the amount of 0.2 to 13% by weight, preferably 0.3 to 3% by weight, more preferably 0.4 to 1% by weight per one preparation.

Potassium carbonate used in this invention is not particular limited, and it is especially preferred to use one having no hydration, such as potassium carbonate anhydride.

To a preparation of this invention, if necessary, various additives ordinally known, such as a vehicle, binding agent, disintegrator, lubricant, thickener, surface active agent, osmotic pressure adjusting agent, electrolyte, sweetening agent, perfume, coloring matter, pH adjusting agent or the like, can be added, in addition to the above iron containing compound and foam components. Examples of vehicles are starches such as wheat starch, potato starch, corn starch, dextrin; saccharides such as sucrose, glucose, fructose, maltose, xylulose, lactose or the like; sugar alcohols such as sorbitol, mannitol, maltitol, xylitol or the like; saccharide-transglycoside such as coupling sugar, palathinose or the like; calcium phosphate; calcium sulfate; or the like. Examples of the binding agents or thickeners are starch, saccharides, gelatin, gum arabic, dextrin, methyl cellulose, CMC-Na, polyvinyl pyrrolidone, polyvinyl alcohol, hydroxypropyl cellulose, xanthan gum, pectin, tragacanth gum, casein, alginic acid, or the like. Examples of lubricants are leucine, isoleucine, L-valine, sugar-ester, hardened oil, stearic acid, magnesium stearate, talc, macrogol or the like. Examples of disintegrators are avicel, CMC, CMC-Ca or the like. Example of surface active agents are polysorbate, lecithin or the like. Examples of sweetening agents are saccharides; sugar alcohols: dipeptides such as aspartame, alitame; stevia; saccharin; or the like.

The suitable amounts of these additives can be determined in view of the relationship between the additives and the essential ingredients, properties of preparation, process for preparing it or the like.

Furthermore, the suitable amount of various vitamines, especially cyanocobalamin, ascorbic acid (vitamine C) or the like, may be added to the preparation. Therefore, it also is possible to supply vitamin to the body. The amount of the vitamin to be added is not limited, and vitamine C may be added at an amount of not exceeding 30% by weight, preferably about 5 to 25% by weight in view of taste.

A preparation of this invention can be not only in the form of a tablet, but also may be in other solid forms such as granule, powder, capsule or the like.

In preparing a preparation of this invention, methods similar to conventional methods employed in respective preparation form may be employed. For example, a tablet form can be prepared by a method for directly pressurizing powders or by a method for dry or wet pressurizing granules, after weighing and mixing the prescribed amount of each ingredient. Also, powder can be prepared by weighing and mixing the prescribed amount of each ingredient followed by folding. Granules can be prepared by drying to form particles followed by folding, after weighing and mixing the prescribed amount of each ingredient.

A preparation of this invention which is in the form of foam tablet or powder is put into water to dissolve or disperse, and then is orally taken. Conversely, the preparation of this invention may be orally taken in its unchanged form followed by drinking water.

Dosage of a preparation of this invention should be calculated by known methods based on which internal organ or organization of the living body is to be imaged, and in general, may be taken by dissolving 1.5 to 6 g of the preparation in 100 to 300 ml of water. In the case of contrast imaging of pancreas, 1 or 2 tablets which are prepared at about 1.5 to 6 g per one tablet are taken by dissolving in 100 to 300 ml of water.

A preparation of this invention can be utilized in NMR diagnosis of the alimentary canal, i.e. walls of alimentary canal such as stomach, duodenum, small intestine, large intestine or the like; or pancreas, liver, peritoneum, mesentery or a like. In this case, the preparation of this invention is suitable to contrast imaging representation between alimentary canal and parenchymal internal organs, whereby $T_1$ value is shortened.

INDUSTRIAL APPLICABILITY

Figure 1:
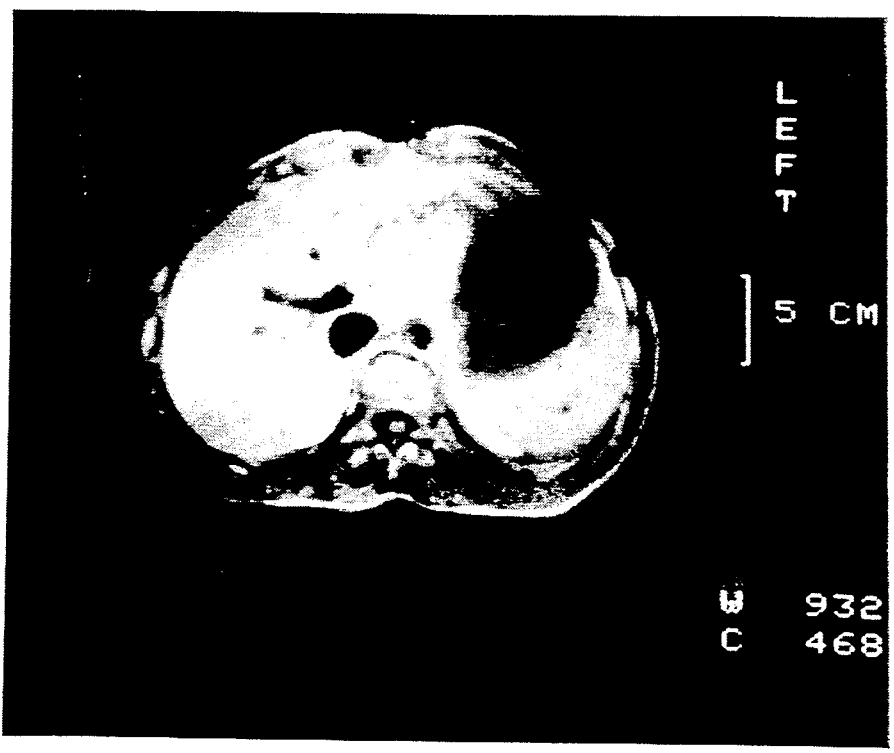
FIG. 1 is a NMR imaging photograph of abdominal part before taking the preparation of Example 1.

As mentioned above, a preparation of this invention makes it possible to take it orally with ease, and to expand and extend alimentary canal by foaming of the foaming ingredients. As a result, form of alimentary canal, the state of its lumen and the relationship between alimentary canal and the surrounding organs can be easily known. Furthermore, a preparation of this invention has an excellent imaging effect enhancing signal strength in the alimentary canal. Thus, it is expected to improve the accuracy of diagnosis of various diseases.

Also, by adding potassium carbonate to the foam preparation, foaming and altertion during preservation can be prevented, and as a result, the preparation of this invention is superior in preservation stability.

EXAMPLES

Examples of this invention are explained below in detail. In each example, "parts" and "%" mean "parts by weight" and "% by weight", respectively, except as otherwise indicated.

EXAMPLE 1

After mixing each ingredient at the ratio shown below, foam tablets (4.3 g per one tablet) were pharmaceutically prepared from the mixture by a method for directly pressurizing powder.

| (Ingredients) | (%) |
|---|---|
| Granulated sugar | 37 |
| L-Ascorbic acid | 12 |
| L-Tartaric acid | 22 |
| Apartame | 0.8 |
| Sodium hydrogencarbonate | 23 |
| Ammonium iron citrate | 3.4 |
| (25 mg/4.3 g as elemental iron) | |
| Cyanocobalamin | trace amount |
| perfume and coloring | proper amount |
| Total | 100 |

EXAMPLES 2 to 8

Foam tablets having compositions shown in Table 1 was prepared by the same method as Example 1.

TABLE 1

| Ingredients | | Example No. | | | | | | |
|---|---|---|---|---|---|---|---|---|
| | | 2 | 3 | 4 | 5 | 6 | 7 | 8 |
| Glanulated sugar | (parts) | 34 | 30 | 26 | 14 | 17 | 39 | 28 |
| L-Ascorbic acid | (parts) | 12 | 12 | 12 | 16 | 16 | 12 | 12 |
| L-Tartaric acid | (parts) | 22 | 22 | 22 | 30 | 30 | 23 | 27 |
| Aspartame | (parts) | 0.8 | 0.8 | 0.8 | 1.0 | 1.0 | 0.8 | 0.8 |
| NaHCO$_3$ | (parts) | 23 | 23 | 23 | 31 | 31 | 20 | 25 |
| Ammonium iron citrate | (parts) | 6.8 | 10.2 | 14 | 6.8 | 3.4 | 3.4 | 6.8 |
| Cyanocobalamin | (parts) | * | * | * | * | * | * | * |
| Perfume and coloring | (parts) | ** | ** | ** | ** | ** | ** | ** |
| Preparation weight (g/one tablet) | | 4.3 | 4.3 | 4.3 | 4.3 | 4.3 | 4.3 | 4.3 |

TABLE 1-continued

| Ingredients | Example No. | | | | | | |
|---|---|---|---|---|---|---|---|
| | 2 | 3 | 4 | 5 | 6 | 7 | 8 |
| Iron content/one tablet (mg) | 50 | 75 | 100 | 50 | 25 | 25 | 50 |

*indicates "a trace amount of cyanocobalamin"
**indicates "a suitable amount of perfume and coloring matter"

EXAMPLES 9 TO 20

The prescribed amount of each ingredient shown in Table 2 was weighed and mixed, and further sweetening agent and perfume are added at suitable amounts. Then, by folding the mixture, foam powders having a weight (mg/one package) shown in the same table were prepared.

It was also recognized that foam tablets obtained in Examples 2 to 11 show the same enhancement as that of each subject number at the same dose of iron as the above test. Accordingly, a foam tablet obtained in each Example can be suitably applied to abdominal diagnosis using NMR.

These test results were confirmed by administering to subjects the foam tablet obtained in each Example and

TABLE 2

| Ingredients | Example No. | | | | | | | | | | | |
|---|---|---|---|---|---|---|---|---|---|---|---|---|
| | 9 | 10 | 11 | 12 | 13 | 14 | 15 | 16 | 17 | 18 | 19 | 20 |
| L-Tartaric acid (mg) | 893 | 893 | 893 | 893 | 893 | 447 | 1786 | 893 | 893 | 447 | 1786 | 1100 |
| NaHCO$_3$ (mg) | 1000 | 1000 | 1000 | 1000 | 1000 | 500 | 2000 | 500 | 2000 | 1000 | 1000 | 1250 |
| Ammonium iron citrate (mg) | 60 | 150 | 300 | 600 | 1200 | 600 | 600 | 600 | 600 | 600 | 600 | 600 |
| Total (mg/one package) | 1953 | 2043 | 2193 | 2493 | 3093 | 1547 | 4386 | 1993 | 3493 | 2047 | 3386 | 2950 |
| Iron content/ one package (mg) | 10 | 25 | 50 | 100 | 200 | 100 | 100 | 100 | 100 | 100 | 100 | 100 |

NMR Imaging Test (I)

1, 1.5, 2 and 2.5 foam tablets (including 25 mg, 37.5 mg, 50 mg and 62.5 mg of iron, respectively) prepared in Example 1 were taken to four healthy and ordinary subjects (Nos. 1 to 4) by dissolving in 140 ml of water respectively. NMR imaging is carried out before and after taking foam tablets. In such a case, photographs of $T_1$ enhancement image (SE 500 to 600/17 m sec.) and $T_2$ enhancement image (SE 2000/23.90 m sec.) were taken. $T_1$ and $T_2$ values were measured from images of SE 500/23 and 2000/23.90 by double point method. Also, as a mesurment equipment, 1.5T MRI (Magnetom) manufactured by Siemens, W. Germany, and 8 to 10 mm of slice thickness and 4 to 5 mm of slice interval were set.

$T_1$ and $T_2$ values in stomach which were obtained by the above test are shown in Table 3.

TABLE 3

| Subject No. | Dose (mg of iron) | Before taking (Stomach) $T_1/T_2$ | After taking (Stomach) $T_1/T_2$ |
|---|---|---|---|
| 1 | 25.0 | 3111/122 | 2213/149 |
| 2 | 37.5 | 3635/193 | 744/179 |
| 3 | 50.0 | 2379/178 | 573/272 |
| 4 | 62.5 | 3305/202 | 565/307 |

Figure 2:
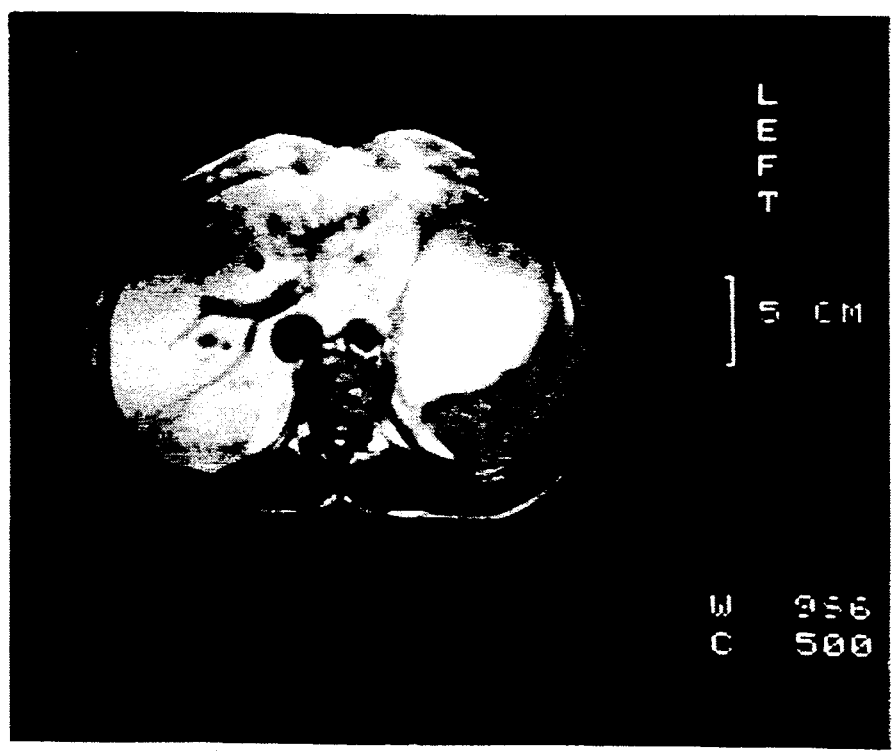
FIG. 2 is a NMR imaging photograph of abdominal part after taking the preparation of Example 1.

The following matter becomes apparent from Table 3. Enhancement of liquid contained in stomach is recognized at all of four doses. Especially, when dose is 25 mg and 62.5 mg of iron, enhancement of liquid contained in stomach is remarkable, and images of stomach wall and pancreas, especially head of pancreas become clear. As to the degree of enhancement, when dose is 50 mg of iron, signal strength of the above liquid contained in stomach is slightly less than that of fatty tissue in abdominal cavity, and therefore the above liquid can be distinguished from the above fat.

taking photographs of abdominal image. That is, as shown in FIG. 1 which is $T_1$ enhancement image of an abdominal part of subject No. 4 before taking, since the inner part of stomach is filled by water and signal is weak, the inner part of stomach is represented by gray or black color, and it is hard to distinguish alimentary canal from other adjacent organs. On the other hand, as shown in FIG. 2 which is $T_1$ enhancement image after taking, time $T_1$ in stomach is shortened, signal strength is increased, and therefore distinction between alimentary canal and other adjacent organs is clear.

Figure 3:
FIGS. 3 and 4 are NMR imaging photographs of abdominal part of the other subject after taking the preparation of Example 1.
Figure 4:

Also, as shown in FIGS. 3 and 4, according to $T_1$ enhancement images after taking, distinction between the alimentary canal and other adjacent organs is clear. Especially, as shown in FIG. 3, the border between pancreas and other internal organs can be clearly confirmed; the head of pancreas which is otherwise difficult to detect anatomically is apparently recognized; other organs such as lung, tail of pancreas, body of pancreas, liver, ren, blood vessel or the like were also recognized clearly; and further stomach wall was clearly identified.

NMR Imaging Test (II)

Figure 5:
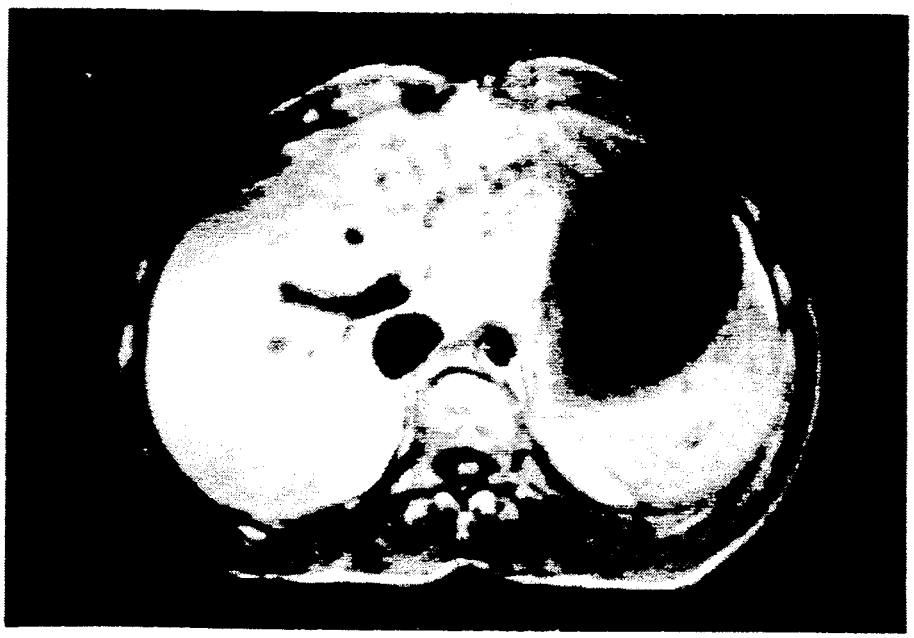
FIG. 5 is a NMR imaging photograph of abdominal part before taking the preparation of Example 20.
Figure 6:
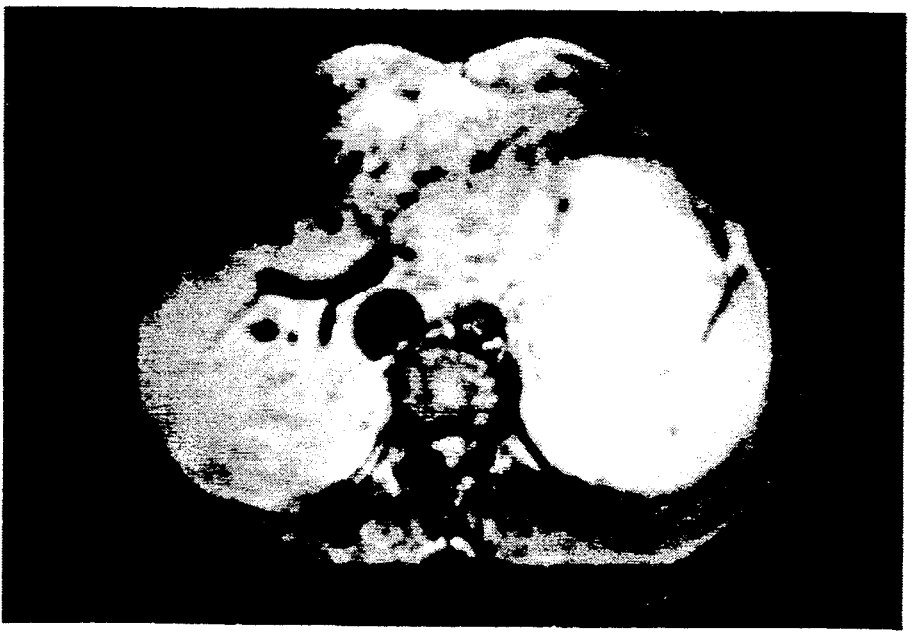
FIG. 6 is a NMR imaging photograph of abdominal part of the other subject after taking the preparation of Example 20.

One package of the foam powder (including 100 mg of iron) prepared in Example 20 was taken by a healthy and ordinary subject by dissolving in 140 ml of water, and further 150 ml of water was given to the subject. FIGS. 5 and 6 are photographs for imaging abdominal part of the subject before and after taking the foam powder. FIG. 5 is $T_1$ enhancement image of stomach part in the condition that water was given to expand alimentary canal. As shown in FIG. 5, signal of water is weak, whereby the inner part of stomach is represented by gray or black color, and distinction between wall and lumen of alimentary canal is unclear. Furthermore, it is difficult to recognize distinction between alimentary canal and the adjacent organs such as pancreas, liver, lung, peritoneum or the like.

On the other hand, signal strength in stomach after taking is increased as shown in $T_1$ enhancement image of FIG. 6, the inner part of stomach is drawn out by white color, and is contrasted to the surrounding organs. Also, as described herein, the stomach wall and the duodenum wall are well recognized, and the tail and head of pancreas are clearly distinguished from the surrounding organs and alimentary canal.

Figure 7:
FIGS. 7 to 9 are NMR imaging photographs of abdominal part of the other subject after taking the preparation of Example 20.

FIG. 7 is $T_1$ enhancement image after taking one package of foam powder obtained by Example 20 with 300 ml of water. In general, it is difficult to take an image of head of pancreas, since its $T_1$ signal approximates to that of duodenum. However, by taking the foam powder of this Example, since the duodenum is expanded and extended by generating carbonic acid gas, and signal strength is increased, head of pancreas can be very clearly drawn out. Similarly, the stomach is fully expanded and extended by water and carbonic acid gas, the border between stomach and body of pancreas is distinct, and contrast is enhanced.

Figure 8:
Figure 9:

It is understood from FIG. 8 that distinction between the wall of duodenum and inner wall is clear, since the duodenum is expanded and extended by generating carbonic acid gas. It is also understood from FIG. 9 that duodenum is expanded and extended from the same reason as FIG. 8.

Accordingly, from the results shown in FIGS. 5 to 9, the form of abdominal organ and relationship between the same and other organs can be accurately and clearly known by taking the foam powder of this Example, whereby it is expected to improve the accuracy of diagnosis against various diseases.

EXAMPLE 21 (including potassium carbonate)

Foam tablet having the composition shown below was prepared by the same manner as Example 1.

| (Ingredients) | (%) |
|---|---|
| Granulated sugar | 40 |
| L-Tartaric acid | 29 |
| Aspartame | 0.8 |
| Sodium hydrogencarbonate | 21 |
| Ammonium iron citrate | 3.6 |
| Potassium carbonate | 0.5 |
| Cyanocobalamin | trace amount |
| Sweetening agent | proper amount |
| Perfume and coloring | proper amount |
| Total | 100 (4.0 g) |

Stability Test

The foam tablet obtained in Example 21 was stored in a constant temperature room kept at 37° C., together with the comparative foam tablet which was prepared by the same manner as that of Example 21 except for not adding potassium carbonate, and a swelling test (by wrapping sheet) discoloration test of tablets, solubility in water and change of taste were examined with time. As a result, the foam tablet of Example 21, with added potassium carbonate had low swell, little discoloration, shorter dissolving time and less change of taste in comparison with the comparative foam tablet, and therefore is superior to the compartive foam tablet in preservation stability.

What is claimed is:

1. A nuclear magnetic resonance imaging method comprising administering a diagnostically effective amount of a contrast medium to a subject and performing nuclear magnetic resonance tomography on said subject, said contrast medium comprising:
   0.1 to 10% by weight, as elemental iron, of at least one iron containing compound selected from the group consisting of an iron (II) salt and an iron (III) salt;
   8 to 60% by weight of at least one of sodium carbonate and sodium hydrogen carbonate; and
   10 to 70% by weight of a neutralizing agent, wherein said neutralizing agent reacts with said at least one of sodium carbonate and sodium hydrogen carbonate to produce carbon dioxide in the alimentary canal of said subject, when orally administered to the subject with water, and wherein the produced carbon dioxide expands and extends the alimentary canal.

2. A method according to claim 1, wherein said iron containing compound is at least one selected from the group consisting of ammonium iron(II) citrate, ammonium iron(III) citrate, sodium iron(II) citrate, sodium iron(III) citrate, iron(II) citrate, iron(III) citrate, iron(II) gluconate, iron(II) pyrophosphate, iron(II) pyrophosphate, iron lactate, iron(II) sulfate, iron(III) chloride, iron sesquioxide, sodium iron chlorophyn, iron(II) fumarate, iron threonine, iron(II) orotinate, saccharated iron oxide, and iron(III) gluconate.

3. A method according to claim 2, wherein said iron containing compound is a trivalent iron salt.

4. A method according to claim 3, wherein said iron containing compound is a trivalent iron citrate salt.

5. A method according to claim 1, wherein said iron containing compound is present in an amount of 0.5 to 5% by weight as elemental iron.

6. A method according to claim 1, wherein said neutralizing agent is selected from the group consisting of L-tartaric acid, citric acid, fumaric acid, lactic acid, malic acid and ascorbic acid.

7. A method according to claim 6, wherein said neutralizing agent is at least one of tartaric acid and citric acid.

8. A method according to claim 1, wherein said preparation, when dissolved in water, has a pH of 3 to 5.5.

9. A method according to claim 8, wherein the pH is 3.5 to 4.6.

10. A method according to claim 1, wherein said preparation comprises 20 to 60% by weight of said at least one of sodium carbonate and sodium hydrogencarbonate.

11. A method according to claim 10, wherein said preparation comprises 8 to 45% by weight of said at least one of sodium carbonate and sodium hydrogen carbonate.

12. A method according to claim 1, wherein said sodium carbonate is present in an amount of 9 to 50% by weight.

13. A method according to claim 12, wherein said sodium carbonate is present in an amount of 22 to 26% by weight.

14. A method according to claim 1, wherein said sodium hydrogen carbonate is present in an amount of 8 to 50% by weight.

15. A method according to claim 14, wherein said sodium hydrogen carbonate is present in an amount of 20 to 45% by weight.

16. A method according to claim 1, wherein said neutralizing agent is present in an amount of 20 to 50% by weight.

17. A method according to claim 16, wherein said neutralizing agent is present in an amount of 30 to 40% by weight.

18. A method according to claim 1, wherein said preparation is in a form capable of being dissolved or dispersed in water.

19. A method according to claim 18, wherein said preparation is in the form of a foaming powder.

20. A method according to claim 18, wherein said preparation is in the form of a foaming tablet.

21. A nuclear magnetic resonance imaging method comprising administering a diagnostically effective amount of a contrast medium to a subject and performing nuclear magnetic resonance tomography on said subject, said contrast medium comprising:
at least one iron containing compound selected from the group consisting of an iron (II) salt and an iron (III) salt
at least one of sodium carbonate and sodium hydrogen carbonate;
a neutralizing agent, and
potassium carbonate as a preservation stabilizing agent; wherein said neutralizing agent reacts with said sodium carbonate or sodium hydrogen carbonate to produce carbon dioxide in the alimentary canal of a subject, when administered to said subject together with water, and wherein said produced carbon dioxide expands and extends said alimentary canal of said subject.

22. A method useful according to claim 21, wherein said potassium carbonate is present in an amount of 0.2 to 13% by weight.

23. A method useful according to claim 22, wherein said potassium carbonate is present in an amount of 0.3 to 3% by weight.

24. A method useful according to claim 23, wherein said potassium carbonate is present in an amount of 0.4 to 1% by weight.

* * * * *